US008900131B2

(12) United States Patent
Chopra et al.

(10) Patent No.: US 8,900,131 B2
(45) Date of Patent: Dec. 2, 2014

(54) MEDICAL SYSTEM PROVIDING DYNAMIC REGISTRATION OF A MODEL OF AN ANATOMICAL STRUCTURE FOR IMAGE-GUIDED SURGERY

(75) Inventors: Prashant Chopra, Sunnyvale, CA (US); Caitlin Q. Donhowe, Sunnyvale, CA (US); Vincent Duindam, Oakland, CA (US); Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 386 days.

(21) Appl. No.: 13/107,562

(22) Filed: May 13, 2011

(65) Prior Publication Data

US 2012/0289777 A1   Nov. 15, 2012

(51) Int. Cl.
*A61B 1/04* (2006.01)
*A61B 5/05* (2006.01)
(Continued)

(52) U.S. Cl.
CPC ..... *A61B 1/00009* (2013.01); *A61B 2019/5217* (2013.01); *A61B 1/00055* (2013.01); *G06T 2207/10068* (2013.01); *A61B 2019/507* (2013.01); *G06T 19/003* (2013.01); *G06T 7/0046* (2013.01); *A61B 1/0051* (2013.01); *A61B 1/2676* (2013.01); *A61B 2019/5295* (2013.01); *A61B 5/0037* (2013.01); *A61B 2019/5261* (2013.01); *A61B 19/5244* (2013.01); *A61B 2017/00323* (2013.01)
USPC ........... 600/117; 600/109; 600/407; 600/424; 600/425

(58) Field of Classification Search
CPC .......... A61B 19/5244; A61B 1/00009; A61B 1/00055; A61B 1/0051; A61B 1/2676; A61B 2019/507; A61B 2019/5217; A61B 2019/5261; A61B 2019/5295; A61B 5/0037; G06T 19/003; G06T 2207/10068; G06T 7/0046

USPC .......................................... 600/407, 424–425
See application file for complete search history.

(56) References Cited

U.S. PATENT DOCUMENTS 5,765,561 A   6/1998   Chen et al.
5,797,849 A   8/1998   Vesely et al.
(Continued)

FOREIGN PATENT DOCUMENTS

EP   1779779 A3   9/2007
EP   2286714 A3   3/2012
WO   2008125910 A2   10/2008

OTHER PUBLICATIONS

Banovac, Filip et al., "Liver Tumor Biopsy in a Respiring Phantom with the Assistance of a Novel Electromagnetic Navigation Device," 2002, pp. 200-207, Springer-Verlag.

(Continued)

*Primary Examiner* — John P Leubecker
*Assistant Examiner* — Arnaldo Torres Diaz

(57) ABSTRACT

A medical system provides navigation assistance to a surgeon so that the surgeon may navigate a flexible medical device through linked passages of an anatomical structure to a target in or adjacent to the anatomical structure. As the medical device moves through the linked passages, images are captured by an image capturing element at its distal end and pose and shape information for the medical device are received from sensors disposed in the medical device. A 4-D computer model of the anatomical structure is registered to the medical device using one or both of 4-D shape registration and virtual camera registration so that the captured image and a virtual image generated from the perspective of a virtual camera are registered to each other and displayed while providing an indication of a navigational path to the target.

30 Claims, 12 Drawing Sheets

(51) Int. Cl.

| | | |
|---|---|---|
| A61B 1/00 | (2006.01) | |
| G06T 19/00 | (2011.01) | |
| G06T 7/00 | (2006.01) | |
| A61B 1/267 | (2006.01) | |
| A61B 19/00 | (2006.01) | |
| A61B 1/005 | (2006.01) | |
| A61B 5/00 | (2006.01) | |
| A61B 17/00 | (2006.01) | |

(56) References Cited

U.S. PATENT DOCUMENTS

| | | | |
|---|---|---|---|
| 6,246,898 B1 | 6/2001 | Vesely et al. | |
| 6,256,090 B1 | 7/2001 | Chen et al. | |
| 6,346,940 B1* | 2/2002 | Fukunaga | 345/427 |
| 6,468,265 B1 | 10/2002 | Evans et al. | |
| 6,522,906 B1 | 2/2003 | Salisbury, Jr. et al. | |
| 6,923,768 B2 | 8/2005 | Camus et al. | |
| 7,233,820 B2 | 6/2007 | Gilboa | |
| 7,398,116 B2 | 7/2008 | Edwards | |
| 7,517,320 B2 | 4/2009 | Wibowo et al. | |
| 7,756,563 B2* | 7/2010 | Higgins et al. | 600/407 |
| 7,772,541 B2* | 8/2010 | Froggatt et al. | 250/227.23 |
| 7,822,461 B2* | 10/2010 | Geiger et al. | 600/415 |
| 7,889,905 B2 | 2/2011 | Higgins et al. | |
| 7,901,348 B2 | 3/2011 | Soper et al. | |
| 8,049,777 B2* | 11/2011 | Akimoto et al. | 348/65 |
| 8,199,984 B2* | 6/2012 | Mori et al. | 382/128 |
| 8,226,560 B2* | 7/2012 | Arai et al. | 600/443 |
| 8,368,746 B2* | 2/2013 | Hirakawa et al. | 348/65 |
| 2002/0087169 A1 | 7/2002 | Brock et al. | |
| 2003/0055410 A1 | 3/2003 | Evans et al. | |
| 2003/0220541 A1 | 11/2003 | Salisbury et al. | |
| 2004/0097806 A1 | 5/2004 | Hunter et al. | |
| 2005/0107679 A1* | 5/2005 | Geiger et al. | 600/407 |
| 2005/0182295 A1 | 8/2005 | Soper et al. | |
| 2005/0182319 A1 | 8/2005 | Glossop | |
| 2005/0197559 A1 | 9/2005 | Boese et al. | |
| 2005/0200324 A1* | 9/2005 | Guthart et al. | 318/568.11 |
| 2005/0261550 A1* | 11/2005 | Akimoto et al. | 600/117 |
| 2006/0058647 A1* | 3/2006 | Strommer et al. | 600/434 |
| 2006/0184016 A1* | 8/2006 | Glossop | 600/434 |
| 2006/0195033 A1* | 8/2006 | Akimoto et al. | 600/429 |
| 2006/0202998 A1* | 9/2006 | Hirakawa et al. | 345/501 |
| 2007/0010743 A1* | 1/2007 | Arai | 600/443 |
| 2007/0135803 A1 | 6/2007 | Belson | |
| 2007/0208222 A1* | 9/2007 | Miyoshi et al. | 600/117 |
| 2007/0293721 A1 | 12/2007 | Gilboa | |
| 2008/0009674 A1* | 1/2008 | Yaron | 600/117 |
| 2008/0118135 A1 | 5/2008 | Averbuch et al. | |
| 2008/0262297 A1 | 10/2008 | Gilboa et al. | |
| 2009/0123111 A1 | 5/2009 | Udd | |
| 2009/0137952 A1 | 5/2009 | Ramamurthy et al. | |
| 2009/0149703 A1* | 6/2009 | Tanaka | 600/103 |
| 2009/0149711 A1* | 6/2009 | Tanaka et al. | 600/152 |
| 2009/0163800 A1* | 6/2009 | Xu et al. | 600/424 |
| 2009/0163810 A1* | 6/2009 | Kanade et al. | 600/443 |
| 2009/0281452 A1* | 11/2009 | Pfister et al. | 600/567 |
| 2009/0292166 A1* | 11/2009 | Ito et al. | 600/109 |
| 2010/0152600 A1 | 6/2010 | Droitcour et al. | |
| 2010/0234857 A1 | 9/2010 | Itkowitz et al. | |
| 2010/0249506 A1 | 9/2010 | Prisco | |
| 2010/0249507 A1* | 9/2010 | Prisco et al. | 600/117 |
| 2010/0256558 A1* | 10/2010 | Olson et al. | 604/95.01 |
| 2010/0286548 A1 | 11/2010 | Lazar et al. | |
| 2010/0295931 A1* | 11/2010 | Schmidt | 348/65 |
| 2011/0015648 A1 | 1/2011 | Alvarez et al. | |
| 2011/0040404 A1* | 2/2011 | Diolaiti et al. | 700/245 |
| 2011/0184238 A1* | 7/2011 | Higgins et al. | 600/117 |
| 2011/0234780 A1* | 9/2011 | Ito et al. | 348/65 |
| 2012/0099768 A1* | 4/2012 | Helm et al. | 382/128 |
| 2012/0289843 A1 | 11/2012 | Chopra et al. | |
| 2013/0303887 A1* | 11/2013 | Holsing et al. | 600/424 |

OTHER PUBLICATIONS

Burschka, Darius et al., "Navigating Inner Space: 3-D Assistance for Minimally Invasive Surgery," Robotics and Autonomous Systems, 2005 pp. 5-26, vol. 52—Issue 1, Elsevier.

Chiu, Adeline M. et al., "3-D Image Guidance for Minimally Invasive Robotic Coronary Artery Bypass," The Heart Surgery Forum, Jun. 8, 2000, vol. 3—No. 3, pp. 224-231.

Coste-Maniere, Ève et al., "Optimal Planning of Robotically Assisted Heart Surgery: First Results on the Transfer Precision in the Operating Room," The International Journal of Robotics Research, 2004, pp. 539-548, vol. 23—Issue 4-5, SAGE Publications.

Doignon, C. et al., "Model-based 3-D pose estimation and feature tracking for robot assisted surgery with medical imaging," published in "From Features to Actions: Unifying Perspectives in Computational and Robot Vision" workshop at the IEEE International Conference on Robotics and Automation, Apr. 2007, 10 pages. Internet: http://hal.archives-ouvertes.fr/docs/00/35/06/47/PDF/2007_wkicra_doignon.pdf.

Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-450, vol. 2, Springer Verlag.

Proceedings of Medicine Meets Virtual Reality II: Interactive Technology & Healthcare: Visionary Applications for Simulation Visualization Robotics, 1994, Elsevier, 275 Total Pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Search Report and Written Opinion for Application No. PCT/US2012/035390, mailed on Nov. 14, 2012, 11 pages.

International Search Report and Written Opinion for Application No. PCT/US2012/065165, mailed on Feb. 8, 2013, 9 pages.

* cited by examiner

MEDICAL SYSTEM PROVIDING DYNAMIC REGISTRATION OF A MODEL OF AN ANATOMICAL STRUCTURE FOR IMAGE-GUIDED SURGERY

FIELD OF THE INVENTION

The present invention generally relates to medical systems and in particular, to a medical system providing dynamic registration of a model of an anatomical structure for image-guided surgery.

BACKGROUND

Image guided surgery helps surgeons navigate medical devices to targets in patients so that therapeutic and/or diagnostic medical procedures may be performed on the targets. For guidance, the pose (i.e., position and orientation) of a working end of a medical device may be tracked and its image displayed along with or superimposed on a model of an anatomical structure associated with the target. The model may be computer generated from pre-operative and/or intra-operative patient anatomy scan data such as x-ray, ultrasound, fluoroscopy, computed tomography (CT), magnetic resonance imaging (MRI), and other imaging technologies. The medical device may be an endoscope, catheter, or medical instrument that has a steerable tip and flexible body capable of conforming to body passages leading to the target in an anatomical structure of the patient.

Displaying the target upon which the therapeutic and/or diagnostic medical procedure is to be performed, the model of the anatomical structure in which the target resides or is adjacent to, and an image of the working end of the medical device superimposed on the model of the anatomical structure may be particularly useful to the surgeon to provide assistance in guiding the medical device through natural and/or artificial body passages to and through the anatomical structure to the target. Proper registration of the model to the medical device, however, may be very difficult when the anatomical structure is neither immobile nor rigid, but instead, moves and/or changes shape according to periodic or non-periodic movement of the anatomical structure such as the case with a patient's lung or beating heart.

OBJECTS AND SUMMARY

Accordingly, one object of one or more aspects of the present invention is a medical system and method implemented therein for providing dynamic registration of a model of an anatomical structure with intra-operative anatomical information for image-guided surgery.

Another object of one or more aspects of the present invention is a medical system and method implemented therein for providing dynamic registration of a model of an anatomical structure with intra-operative anatomical information for image-guided surgery that are simple to implement and do not require an expensive tracking system.

Another object of one or more aspects of the present invention is a medical system and method implemented therein for providing dynamic registration of a model of an anatomical structure during image-guided surgery that are computationally efficient and suitable for real-time applications.

Another object of one or more aspects of the present invention is a medical system and method implemented therein for providing dynamic registration of a model of an anatomical structure during image-guided surgery that are accurate.

These and additional objects are accomplished by the various aspects of the present invention, wherein briefly stated, one aspect is a medical system comprising: a memory storing information of a computer model of an anatomical structure; a medical device having a flexible body and a plurality of sensors distributed along the length of the flexible body; and a processor programmed to determine the pose and shape of the flexible body while disposed in a passage of the anatomical structure using information provided by the plurality of sensors at the same point in time and register the computer model to the medical device by matching at least the determined shape of the flexible body to a best fitting one of the shapes of one or more potential passages in the computer model of the anatomical structure.

Another aspect is a method for registering a computer model of an anatomical structure with a flexible medical device disposed within a passage in the anatomical structure, wherein the flexible medical device has a plurality of sensors distributed along the length of the flexible medical device, the method comprising: determining a current pose and shape of the flexible medical device using information provided by the plurality of sensors at the same point in time; registering the computer model of the anatomical structure to the flexible medical device by matching at least the determined shape of the flexible medical device to a best fitting one of the shapes of potential passages in the computer model.

Another aspect is a medical system comprising: a memory storing information of a computer model of an anatomical structure; a medical device; an image capturing device for capturing images from a perspective of a distal end of the medical device; and a processor programmed to periodically perform a global registration of the computer model to the medical device by determining the pose and shape of the medical device while disposed in a passage of the anatomical structure and matching at least the determined shape of the medical device to a best fitting one of the shapes of one or more potential passages in the computer model of the anatomical structure, followed by performing a local registration of the computer model to the medical device by comparing an image captured by the image capturing device with a plurality of virtual views of the computer model of the anatomical structure, wherein the plurality of virtual views is generated from the perspective of a virtual camera whose pose is initially set at the pose of the distal end of the medical device and then perturbed about the initial pose.

Still another aspect is a method for registering a computer model of anatomical structure to a medical device, the method comprising: periodically performing a global registration of the computer model to the medical device by determining the pose and shape of the medical device while disposed in a passage of the anatomical structure and matching at least the determined shape of the medical device to a best fitting one of the shapes of one or more potential passages in the computer model of the anatomical structure, followed by performing a local registration of the computer model to the medical device by comparing an image captured by the image capturing device with a plurality of virtual views of the computer model of the anatomical structure, wherein the plurality of virtual views is generated from the perspective of a virtual camera whose pose is initially set at the pose of the distal end of the medical device and then perturbed about the initial pose.

Additional objects, features and advantages of the various aspects of the present invention will become apparent from the following description which should be taken in conjunction with the accompanying drawings.

DETAILED DESCRIPTION

Figure 1:
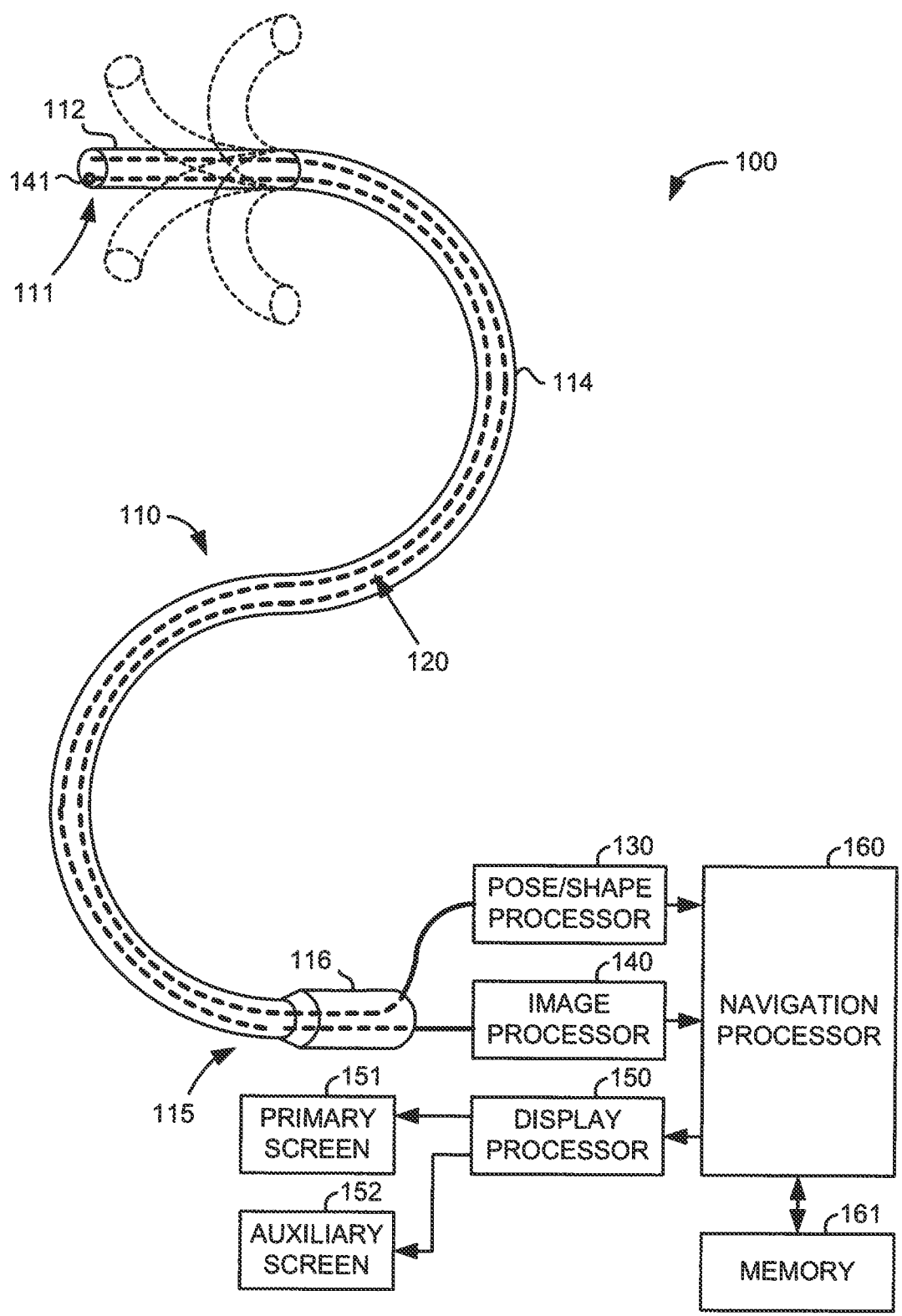
FIG. 1 illustrates a medical system, utilizing aspects of the present invention, which includes a hand-operated medical device.

FIG. 1 illustrates, as an example, a medical system 100 including a steerable medical device 110, one or more fiber optic cables 120 inserted in the medical device 110, a pose/shape processor 130, an image processor 140, an image capturing element 141, a display processor 150, a primary display screen 151, an auxiliary display screen 152, a navigation processor 160, and memory 161. Although shown as separate units, the pose/shape processor 130, image processor 140, display processor 150, and navigation processor 160 may each be implemented as hardware, firmware, software or a combination thereof, which interact with or are otherwise executed by one or more computer processors. The primary and auxiliary display screens, 151 and 152, are preferably computer monitors capable of displaying three-dimensional images to an operator of the system 100. However, for cost considerations, either or both of the primary and auxiliary display screens, 151 and 152, may be a standard computer monitor capable of only displaying two-dimensional images.

The medical device 110 has a flexible body 114, a steerable tip 112 at its distal end 111, and a hand-operable handle 116 at its proximal end 115. Control cables (not shown) or other control means typically extend from the handle 116 to the steerable tip 112 so that the tip 112 may be controllably bent or turned as shown for example by dotted line versions of the bent tip 112. The medical device 110 may be an endoscope, catheter or other medical instrument having a flexible body and steerable tip.

The image capturing element 141 may be a stereoscopic or monoscopic camera disposed at the distal end 111 for capturing images that are transmitted to and processed by the image processor 140 and/or display processor 150 and displayed on the primary display screen 151, auxiliary display screen 152, and/or other display means according to the various aspects of the invention as described herein. Alternatively, the image capturing element 141 may be a coherent fiber-optic bundle that couples to an imaging and processing system on the proximal end of the medical device 110, such as a fiberscope. The image capturing element 141 may also be single or multi-spectral that captures image data in the visible or infrared/ultraviolet spectrum. Thus, any image capturing element, device, or system referred to herein may be any one or a combination of these and other imaging technologies. One of a plurality of fiber optic cables 120 may be coupled at its proximal end to a light source (not shown) for illumination purposes at the distal end 111. Others of the fiber optic cables 120 may be configured with position and bend or shape sensors such as Fiber Bragg Gratings (or other strain sensors such as those employing Rayleigh scattering) distributed along the length of the medical device 110 so that light passing through the fiber optic cable is processed by the pose/shape processor 130 to determine a current pose and shape of the medical device 110.

Figure 2:
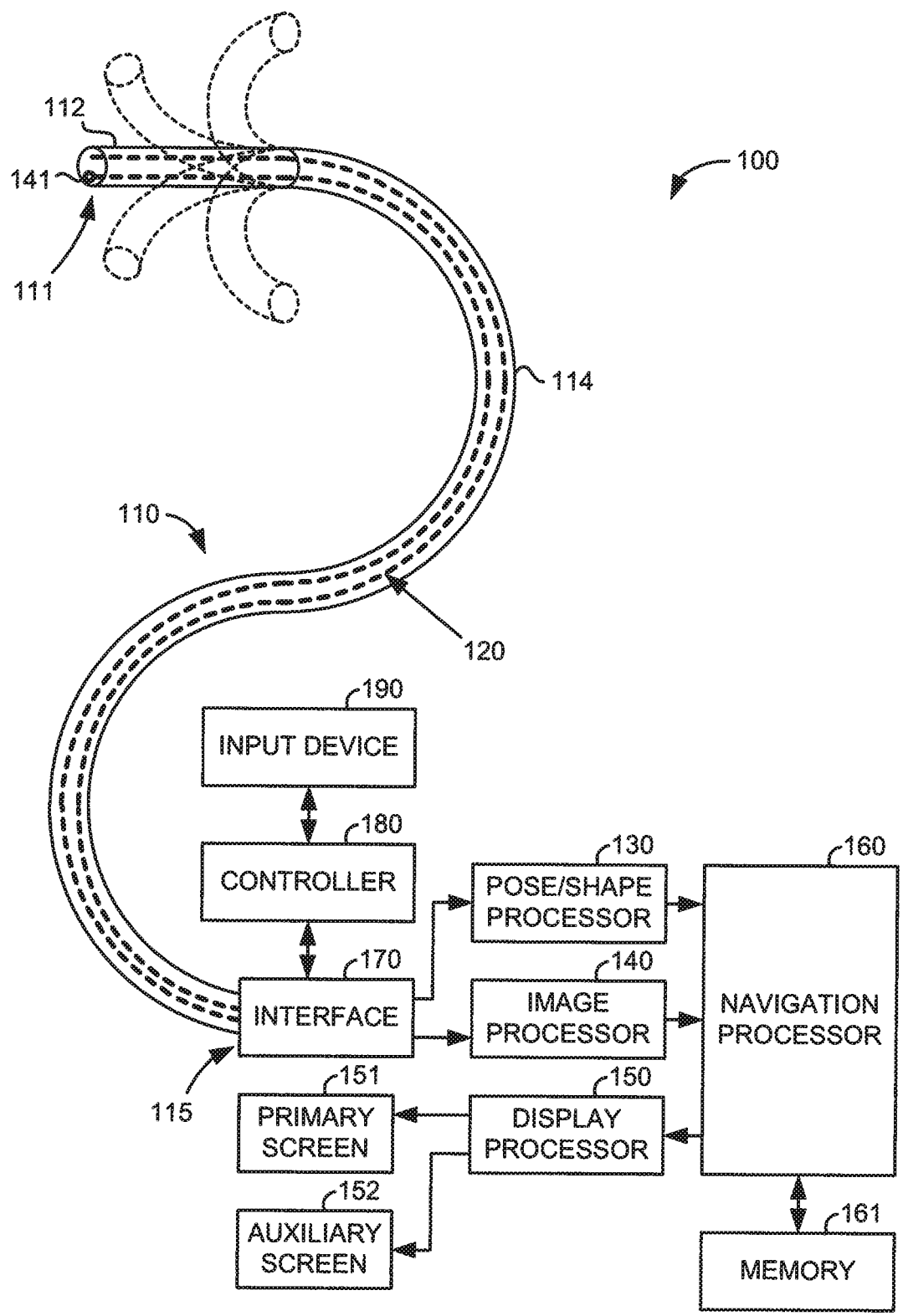
FIG. 2 illustrates an alternative medical system, utilizing aspects of the present invention, which includes a teleoperated medical device.

FIG. 2 illustrates, as an example, an alternative embodiment of the medical system 100 in which the handle 116 is replaced by an electromechanical interface 170, controller 180, and input device 190 for teleoperating the medical device 110. The interface 170 includes actuators for actuating cables in the medical device 110 to steer its tip 112 as well as an actuator for moving the entire medical device 110 forward and backward so that it may be inserted into and retracted out of a patient through an entry port such as a natural body orifice or a surgeon created one. The controller 180 is preferably implemented as hardware, firmware or software (or a combination thereof) in the same one or more computer processors as the processors 130, 140, 150, and 160, or a different computer processor. The flexible body 114 may be passively or actively bendable in this embodiment.

Examples of such steerable medical devices are described in U.S. 2010/0249506 A1 entitled "Method and System for Assisting an Operator in Endoscopic Navigation" and WO 2009/097461 A1 entitled "Apparatus and Methods for Automatically Controlling an Endoscope, which are each incorporated herein by reference. Details on the determination of the endoscope's position and bending using Fiber Bragg Gratings may be found, for examples, in U.S. 2007/0156019 A1 entitled "Robotic Surgery System Including Position Sensors Using Fiber Bragg Gratings", U.S. 2008/0212082 A1 entitled "Fiber Optic Position and/or Shape Sensing Based on Rayleigh Scatter", U.S. 2008/0218770 A1 entitled "Robotic Surgical Instrument and Methods using Bragg Fiber Sensors", and U.S. 2009/0324161 A1 entitled "Fiber Optic Shape Sensor", which are each incorporated herein by reference.

Figure 3:
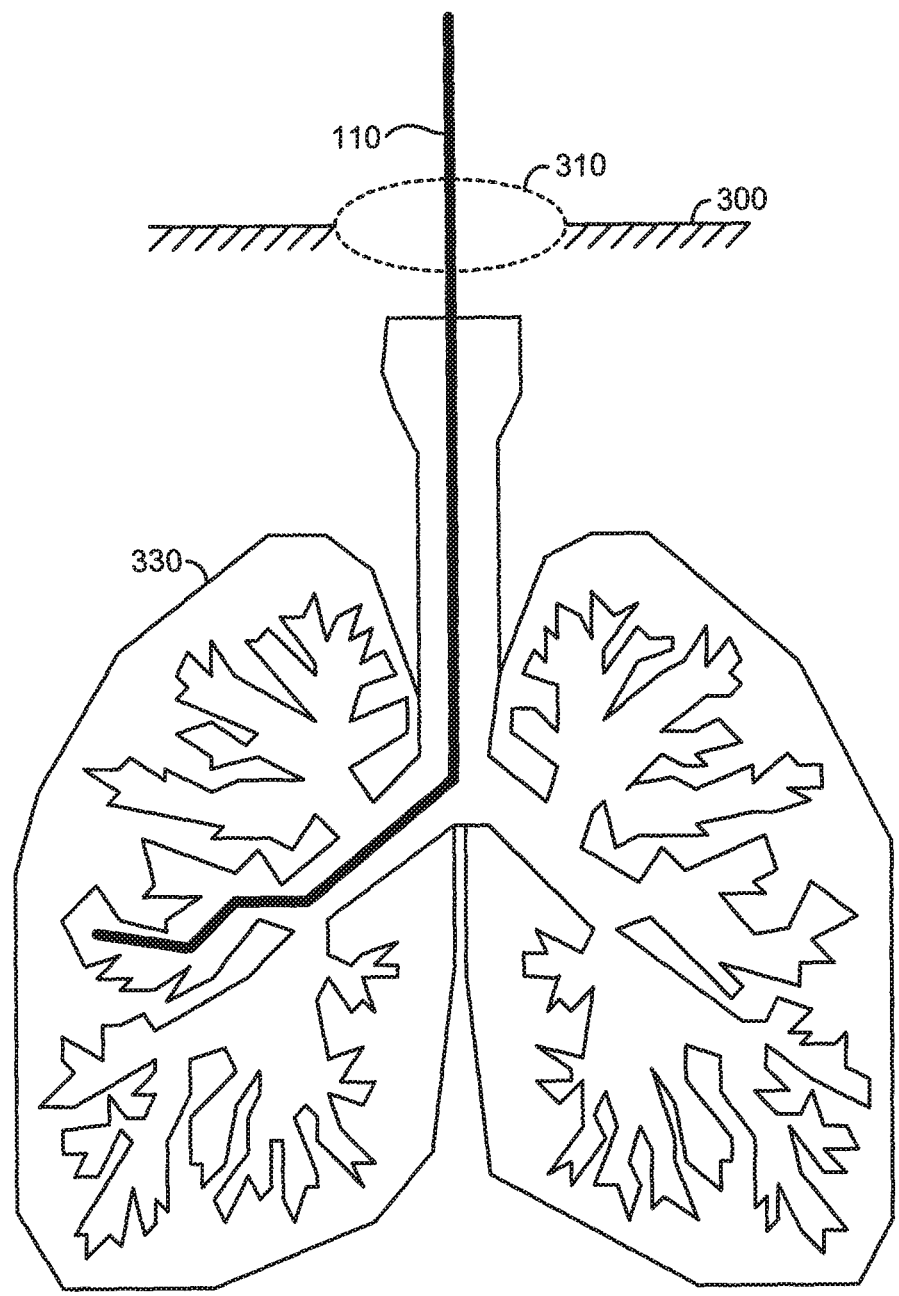
FIG. 3 illustrates a diagram of a medical device inserted into an anatomical structure of a patient.

FIG. 3 illustrates, as an example, a diagram of a medical device 110 inserted through an entry port 310 and extending into an anatomical structure 330 of a patient 300. In this example, the anatomical structure 330 is a pair of lungs having a plurality of natural body passages including a trachea, bronchi, and bronchioles; the entry port 310 is the patient's mouth; and the medical device 110 is a bronchoscope. Due to the nature of the lung, the medical device 110 may be guided through a number of linked passages of the bronchial tree. In doing so, the flexible body 114 of the medical device 110 conforms to the passages through which it travels. Although a pair of lungs is shown in the present example, it is to be appreciated that the various aspects of the present invention are also applicable and useful for other anatomical structures such as the heart, brain, digestive system, circulatory system, and urinary system, in addition to the respiratory system. Further, although only natural body passages are shown, the methods described herein are also applicable to artificial or surgeon created passages that may be formed during or prior to a medical procedure and superimposed on the computer model of the patient anatomy.

Figure 4:
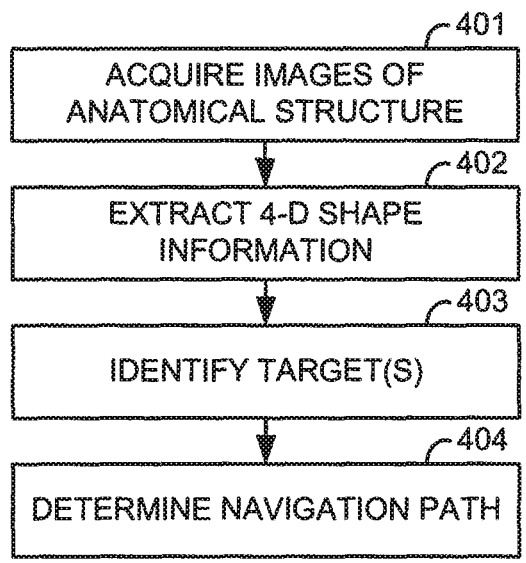
FIG. 4 illustrates a flow diagram of preoperative tasks conducted prior to performing a medical procedure on a patient.

FIG. 4 illustrates, as an example, a flow diagram of preoperative tasks that are performed in preparation for a medical procedure on a patient. In the following example, the anatomical structure is presumed to be one that moves during a medical procedure in an identifiable way such as periodic motion of the air and blood circulatory systems or a non-periodic motion such as a body response to a stimulus. Although aspects of the invention may still be applicable and useful when the anatomical structure does not move during a medical procedure, the full advantages of the present invention are best experienced in an environment in which the anatomical structure moves in an identifiable or otherwise known manner during the medical procedure.

In block 401, one or more sets of images of a patient is acquired using an appropriate imaging technology from which a set of three-dimensional (3-D) computer models of the anatomical structure may be generated, wherein each 3-D computer model is associated with a different point in time over a period of time so that time represents a fourth dimension and the images are referred to herein as four-dimensional (4-D) images. Additional dimensions may also be defined and used in the methods described herein. Examples of such an imaging technology include, but are not limited to, fluoroscopy, Magnetic Resonance Imaging, thermography, tomography, ultrasound, Optical Coherence Tomography, Thermal Imaging, Impedance Imaging, Laser Imaging, nano-tube X-ray imaging, etc.

Figure 5:
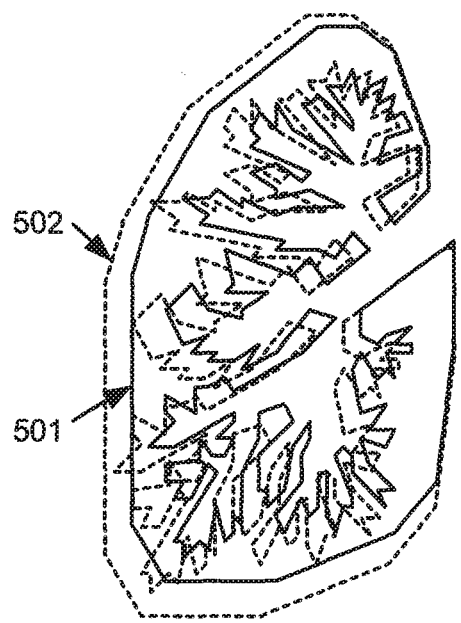
FIG. 5 illustrates movement of a lung during a respiratory cycle.

The period of time over which images are captured depends upon the anatomical structure and the motion of interest. For example, when the anatomical structure is the lungs, one set of images may be for a periodic motion such as a respiratory cycle shown in FIG. 5 where the lung expands from a maximum exhalation state 501 (solid lines) to a maximum inhalation state 502 (dotted lines). Another set of images may be for a non-periodic motion such as a cough or other body reaction to a stimulus resulting in movement of the lungs. As another example, when the anatomical structure is the heart, one set of images may be for a periodic motion such as a blood circulatory cycle. The sampling rate which determines the number of such 3-D computer models is chosen so that the movement of the anatomical structure during such period of motion is adequately described for accurate registration and navigation purposes.

In block 402, 4-D shape information is extracted from the acquired images of the anatomical structure. When the acquired images are sets of two-dimensional (2-D) slices of the anatomical structure sampled at incremental points in time (e.g., according to a sampling rate) over the period of motion, 3-D shape information for the anatomical structure is generated for each set of 2-D slices corresponding to the same point in time. Thus, for n-points in time, "n" sets of 3-D shape information are extracted, where "n" is the number of sampling points in time over the period of motion.

In block 403, one or more targets are identified in the anatomical structure. The targets are locations or objects in or adjacent to the anatomical structure where or upon which a medical procedure is to be performed. For example, the target may be a tumor in or adjacent to the anatomical structure. The target(s) may be identified by a surgeon in a conventional manner by analysis of the acquired images of the anatomical structure or the extracted 4-D shape information, whichever is more convenient and/or reliable for such identification.

In block 404, a navigational path is determined to and through the anatomical structure for the working end of the medical device 110 to travel to each target. In this case, the working end is assumed to be the distal end 111 of the medical device 110. The surgeon may determine a suitable navigational path to a target by analyzing the acquired images of the anatomical structure or the extracted 4-D shape information so as to take into account any damage to the patient that the medical device 110 may cause as it moves towards the target as well as the shortest time and/or shortest path. Alternatively, a computer program may cause a processor to perform such analysis to determine the navigational path using artificial intelligence techniques.

Figure 6:
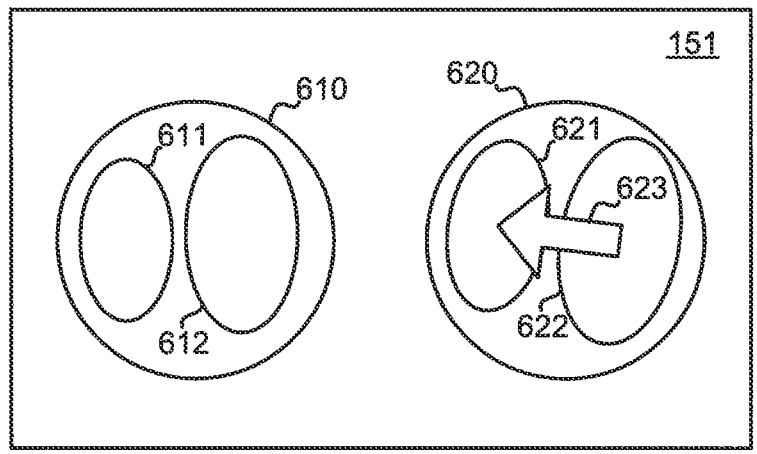
FIG. 6 illustrates a view of a primary screen during navigation of a medical device to a target area in an anatomical structure before registration of a computer model of the anatomical structure to the medical device.

FIG. 6 illustrates, as an example, a view of the primary screen 151 during navigation of the medical device 110 to a target area in an anatomical structure before registration of a computer model of the anatomical structure to the medical device. A left image 610 is the image captured by the image capturing element 141 while viewing a bifurcation in a lung, wherein the bifurcation indicates a left passage 611 and a right passage 612 through which one or the other the medical device 110 may pass through as it is inserted further into the lung. Also shown is a right image 620 which is a virtual image generated by a virtual camera viewing a corresponding location in a 4-D computer model of the anatomical structure which has been generated from the 4-D shape information extracted in block 402 of FIG. 4 before the 4-D computer model is registered in some fashion to the medical device 110. In particular, although left 621 and right 622 passages corresponding to the passages 611 and 612 are shown, their sizes and alignments differ due to translational and rotational errors in the registration transformation relating the 4-D computer model of the anatomical structure to the medical device 110.

Figure 7:
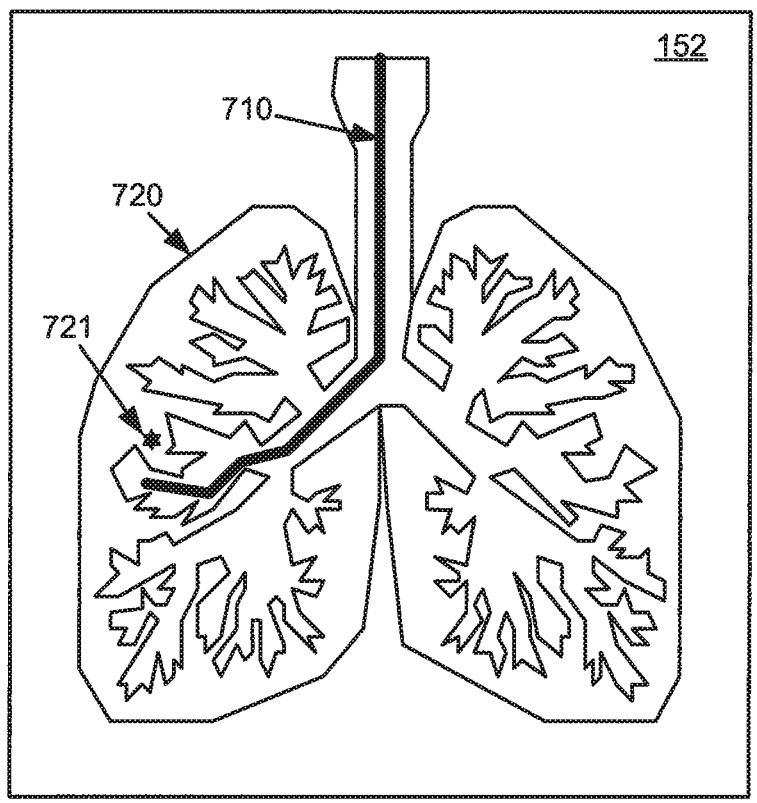
FIG. 7 illustrates a view of an auxiliary screen during navigation of a medical device to a target area in an anatomical structure.

FIG. 7 illustrates, as an example, a view of the auxiliary screen 152 during navigation of the medical device 110 to a target area in an anatomical structure. The view may be either a 2-D or 3-D view of a computer model 720 of the anatomical structure 330 and a computer model 710 of the medical device 110, which is updated in real-time as the medical device 110 moves through the anatomical structure 330. Also shown is an indication 721 of the target. Thus, the auxiliary screen 152 assists the surgeon to steer the medical device 110 through the anatomical structure 330 to the target.

Figure 8:
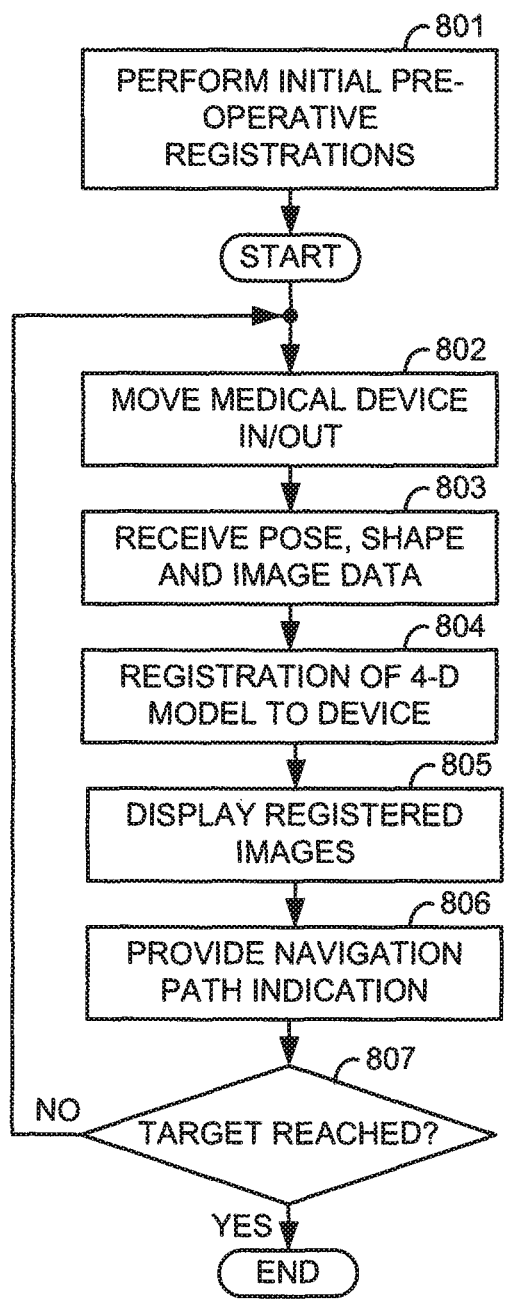
FIG. 8 illustrates a flow diagram of a method for performing a medical procedure including one of a first and second method, utilizing aspects of the present invention, for registering a computer model of an anatomical structure with a medical device.

FIG. 8 illustrates, as an example, a flow diagram of a method for performing a medical procedure on a patient. In block 801, a number of pre-operative tasks are performed in preparation of performing the medical procedure. First, the medical device 110 is localized to a fixed reference frame in a conventional manner by, for example, touching the distal end 111 of the medical device 110 to a known and stationary point in the fixed reference frame. Second, the patient may be registered to the fixed reference frame in a conventional manner by touching and holding the distal end 111 of the medical device 110 to one or more points on the patient, which points correspond to identifiable points on the acquired images of the patient as described in block 401 of FIG. 4, during the period of motion associated with the 4-D computer model. Thus, by applying known relationships between the one or more points on the patient to the anatomical structure 330, the computer model of the anatomical structure may be registered to the anatomical structure of the patient, the fixed reference frame, and the medical device 110.

Navigation of the medical device 110 through the linked passages of the anatomical structure 330 to the target is performed from START to END in FIG. 8. In block 802, the medical device 110 is moved through the linked passages in either the insertion or retraction direction by the surgeon either manipulating the handle 116 or the input device 190, depending upon the embodiment of the medical system 100 being used by the surgeon. In block 803, the navigation processor 160 receives pose and shape information for the medical device 110 from the pose/shape processor 130 and image data from the image processor 140. Thus, the navigation processor 160 has information on the current position and orientation (i.e., pose) of the distal end 111 of the medical device 110 and the shape of the flexible body 114 of the medical device 110 along with an image that has been captured by the image capturing element 141 at that time.

In block 804, the navigation processor 160 performs a correction to the registration of the 4-D computer model of the anatomical structure 330 to the medical device 110. One method for performing this registration is described in reference to FIG. 9 and another method is described in reference to FIG. 10. Alternatively, rather than performing one or the other of the two methods, both methods may be performed as shown and described in reference to FIG. 11. In performing block 804, it is assumed that the shape of the medical device 110 conforms to the shape of the passage of the anatomical structure in which the medical device 110 is disposed at the time. Therefore, registration of the computer model to the medical device 110 effectively registers the computer model of the anatomical structure to the actual anatomical structure of the patient.

Figure 14:
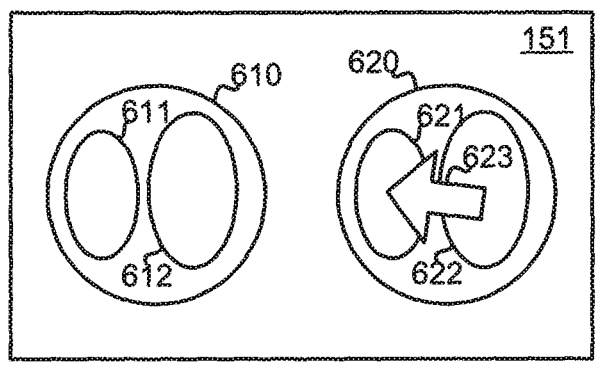
FIG. 14 illustrates a view of a primary screen during navigation of a medical device to a target area in an anatomical structure after registration of a computer model of the anatomical structure to the medical device.

In block 805, the captured image and virtual image are displayed in a similar manner as shown and described in reference to FIG. 6 except that the virtual image 620 is now adjusted to resemble that of the captured image 610, such as shown in FIG. 14, due to the proper registration of the 4-D computer model of the anatomy 330 to the medical device 110. In particular, the size and orientations of the left and right passages, 621 and 622, of the virtual image 620 match those of the left and right passages, 611 and 612, of the captured image 610. In block 806, a navigational path indication such as the arrow 623 in the virtual image 620 is provided so that the surgeon knows that the medical device 110 is to be steered into the indicated passage.

In block 807, a determination is made whether the working end 111 of the medical device 110 has come within a threshold distance to the target. The threshold distance in this case is a distance that is sufficient so that the working end 111 of the medical device 110 can be manipulated by the surgeon to perform its intended purpose without requiring further insertion of the medical device 110 into the anatomical structure 330. If the determination in 807 is YES, then the guided navigation to the target is completed and the method ends. On the other hand, if the medical device 110 has not reached the threshold distance to the target, then the method jumps back to 802 so that the medical device 110 is moved further through the linked passages by the surgeon either manipulating the handle 116 or the input device 190, depending upon the embodiment of the medical system 100 being used by the surgeon.

Figure 9:
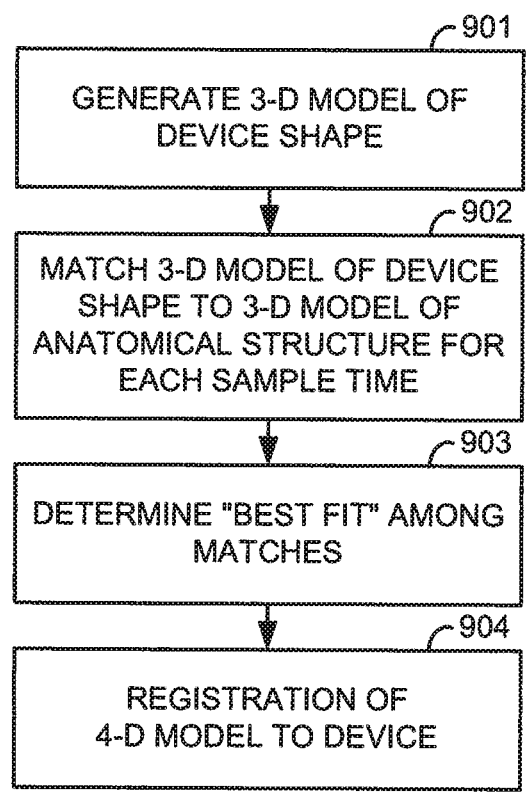
FIG. 9 illustrates a flow diagram of a first method, utilizing aspects of the present invention, for registering a computer model of an anatomical structure with a medical device.

FIG. 9 illustrates, as an example, a flow diagram of a first method (referred to as "shape registration") performable by the navigation processor 160 for registering a computer model of an anatomical structure with a medical device. This method is particularly useful when real-time images are unavailable from the perspective of the distal end 111 of the medical device 110, such as when the image capturing element 141 is either removed or its view is obstructed.

Figure 12A:
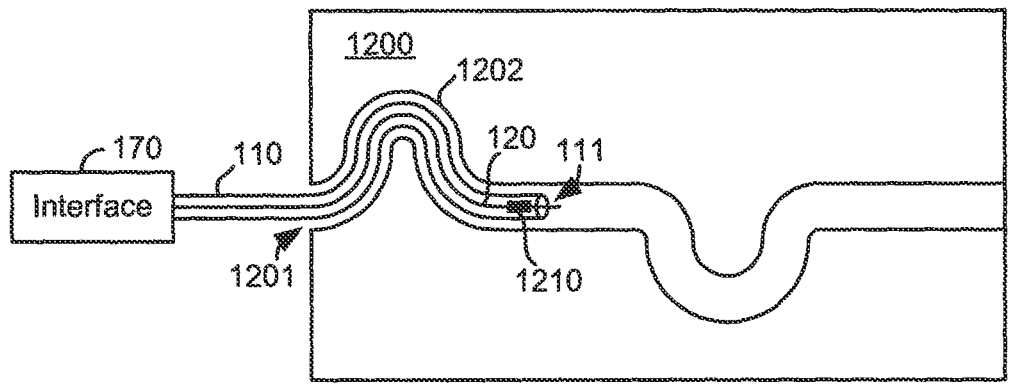
FIGS. 12A-C illustrate schematic drawings of a medical device having a single end sensor respectively at three different points in time as the medical device moves through a passage of an anatomical structure in a patient.
Figure 12B:
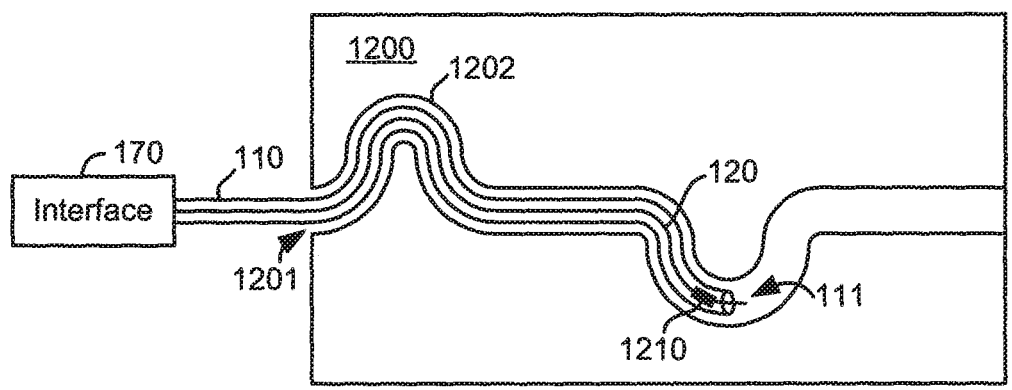
Figure 12C:
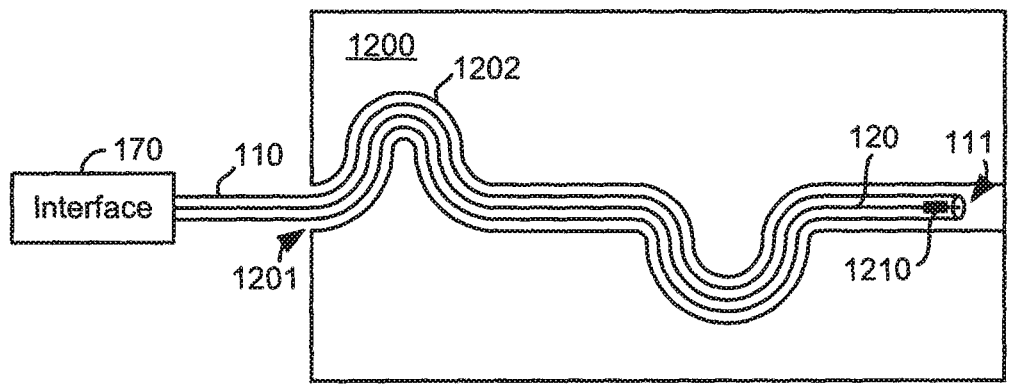
Figure 13:
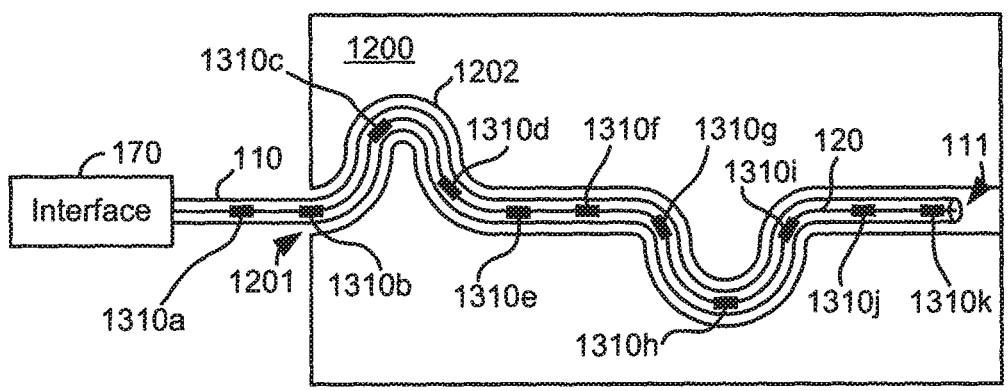
FIG. 13 illustrates a schematic drawing of a medical device having a plurality of distributed sensors at a single point in time while the medical device is disposed in a passage of an anatomical structure in a patient.

As previously explained, since the flexible body 114 conforms to the shape of the passage of the anatomical structure through which the medical device 110 is passing through at the time, the shape of the medical device 110 resembles that of the passage. Thus, by registering the computer model of the anatomical structure to the medical device 110, this is effectively the same as registering the computer model of the anatomical structure to the actual anatomical structure. Alternatively, the shape of the passage might be determined using an approach as described in reference to FIGS. 12A-C, where the pose of a distal end sensor 1210 is recorded at different points in time as the medical device 110 moves through the passage 1202 of an anatomical structure 1200. One problem with this approach, however, is that when the anatomical structure 1200 is moving, the different position measurements which are made at different points in time (and possibly different points in the dynamic movement of the anatomical structure), can lead to errors or complicated correctional adjustments. Therefore, a preferred embodiment of the present invention is shown in FIG. 13, where a plurality of sensors 1310a-1310k are employed that are sufficient in number and properly distributed along the length of the medical device 110 so that all pose and shape measurements may be accurately made at the same point in time.

In block 901, a 3-D computer model corresponding to the current pose and shape of the medical device 110 is generated using the pose and shape information received from the pose/shape processor 130. Since the pose and shape information is readily generated from position and shape sensors disposed in the medical device 110, a computationally fast determination of the medical device's pose and shape is made.

In block 902, the shape of the medical device 110 is compared against shapes of the linked passages in the 3-D computer model for each sampled point in time to find a closest match of linked passages. A number of well-known matching techniques may be used to perform this function such as an Iterative Closest Point (ICP) algorithm or a Singular Value Decomposition (SVD) algorithm as described, for example, in U.S. 2005/0182319 A1, which is incorporated herein by reference. Thus, for each sample time in a dynamic motion cycle, a closest match of the current shape of the medical device 110 (and consequently the passage in which it is disposed at the time) and one of the linked passages in a computer model of the anatomical structure is determined.

In block 903, deviations are determined between each closest match of linked passages determined in 902 and the shape of the medical device 110. The closest match of linked passages having the smallest deviation with the current shape of the medical device 110 is then determined to be the "best fit" among the matches. Thus, whereas block 902 determines for each 3-D computer model, the closest match between one or more of its passages with the current shape of the medical device, block 903 determines the 3-D computer model whose closest match of linked passages is the "best fit" (i.e., closest match) of the closest matches of all the 3-D computer models. In 904, the "best fit" of linked passages in the 4-D computer model of the anatomical structure is then localized to the portion of the medical device 110 which it has been determined to be the "best fit" so that the 4-D computer model is registered to the medical device 110 (and consequently, the anatomical structure of the patient).

Figure 10:
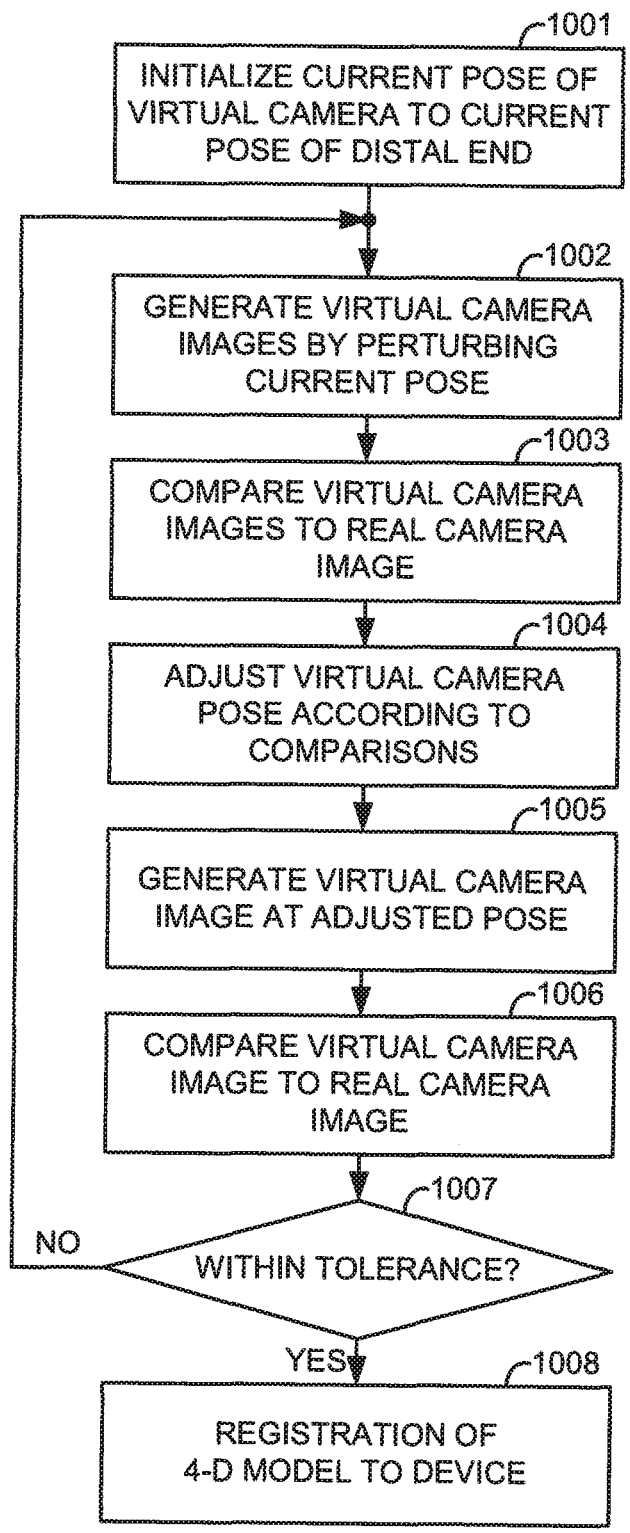
FIG. 10 illustrates a flow diagram of a second method, utilizing aspects of the present invention, for registering a computer model of an anatomical structure with a medical device.

FIG. 10 illustrates, as an example, a flow diagram of a second method (referred to as "virtual camera registration") performable by the navigation processor 160 for correcting the registration of a computer model of an anatomical structure with a medical device. In performing the method, it is assumed that a prior registration of the 4-D computer model and the medical device 110 has been performed (such as initially in block 801 of FIG. 8).

In block 1001, a virtual camera is initially assumed to be disposed at the current pose of the distal end of the medical device 110. In block 1002, one or more virtual images of the 4-D computer model of the anatomic structure are generated as though being captured by the virtual camera by perturbing the current pose of the virtual camera translationally and/or orientationally. In block 1003, the one or more virtual images are compared with the current image of the anatomical structure captured by the image capturing element 141. In block 1004, the virtual camera pose is adjusted according to the comparisons performed in block 1003 so that a virtual image captured by the virtual camera at the adjusted pose will better match the current image of the anatomical structure captured by the image capturing element 141. In block 1005, a virtual image of the 4-D computer model is generated as though being captured by the virtual camera at the adjusted pose. In block 1006, the virtual image captured by the virtual camera at the adjusted pose is compared to the current image of the anatomical structure captured by the image capturing element 141. In block 1007, a determination is made whether the deviation between the virtual image and the real captured image is within a tolerance range. The tolerance range may be pre-set to limit values previously determined in some fashion to result in acceptable matches within a reasonable time period. Alternatively, an algorithm may be used to incrementally change an initial tolerance range as a function of the results of the processing through the loop of blocks 1002-1007.

If the determination is YES, then in 1008, the adjusted pose of the virtual camera is used to generate a registration transform to register the 4-D computer model of the anatomical structure to the medical device 110 and the registration transform is used to localize the 4-D computer model to the medical device 110. On the other hand, if the determination is NO, then the method jumps back to block 1002 to generate one or more virtual images of the 4-D computer model of the anatomic structure from the perspective of the virtual camera by perturbing the adjusted pose of the virtual camera. The method then continues to loop through blocks 1002-1007 until the determination in block 1007 is YES.

Figure 11:
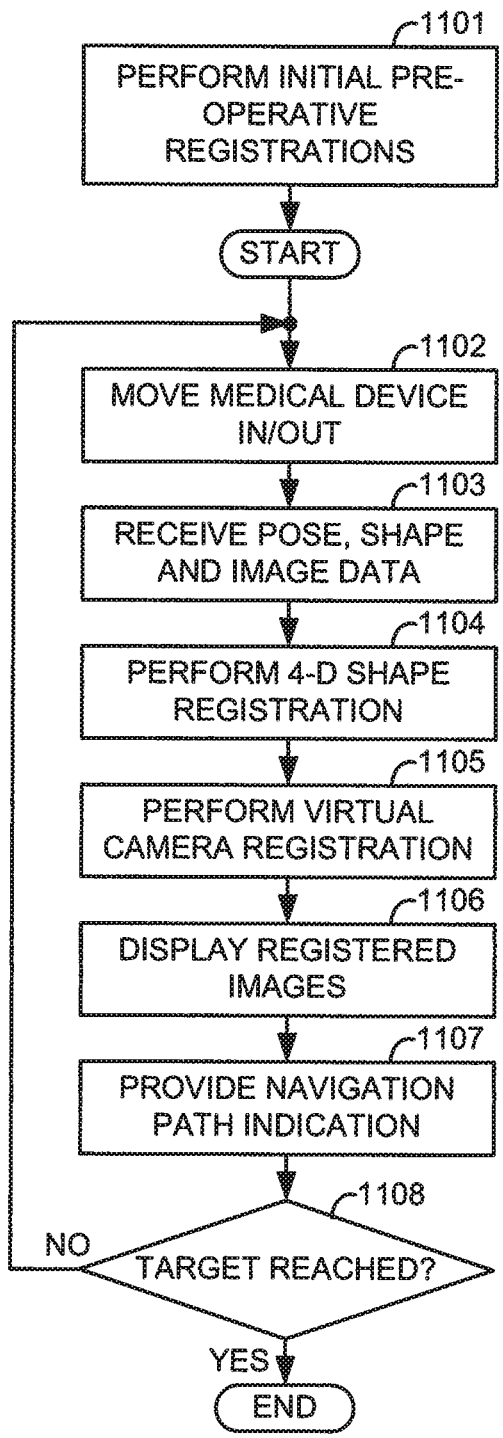
FIG. 11 illustrates a flow diagram of a method for performing a medical procedure including both a first and second method, utilizing aspects of the present invention, for registering a computer model of an anatomical structure with a medical device.

FIG. 11 illustrates, as an example, a flow diagram of a method for performing a medical procedure including both a first and second method for registering a computer model of an anatomical structure with a medical device. In this method, blocks 1101-1103 are performed identically to blocks 801-803 of FIG. 8 and blocks 1106-1108 are performed identically to blocks 805-807 of FIG. 8. Block 1104 is performed identically as the method described in reference to FIG. 9 and may be thought of as a global or coarse registration that is relatively fast to execute. Block 1105 is performed identically to the method described in reference to FIG. 10 and may be thought of as a local or fine registration that corrects for any "residual errors" that may remain after performance of block 1104. Thus, in this example, periodically performing the combination of the methods described in reference to FIGS. 9 and 10 may provide a more accurate registration of the 4-D computer model of the anatomical structure to the medical device 110. Further, periodically performing the global registration of block 1104 may serve to prevent any "drift" errors that may result by only periodically performing block 1105 after an initial registration such as block 801 of FIG. 8.

After performing any of the registration methods described herein, if the resulting virtual image 620 is still visibly misaligned with the captured image 610 (such as viewed on the primary display screen 151), manual registration means may be provided whereby the computer model may be translated and/or oriented according to operator manipulation of an input device until the virtual and captured images appear aligned.

Figure 15:
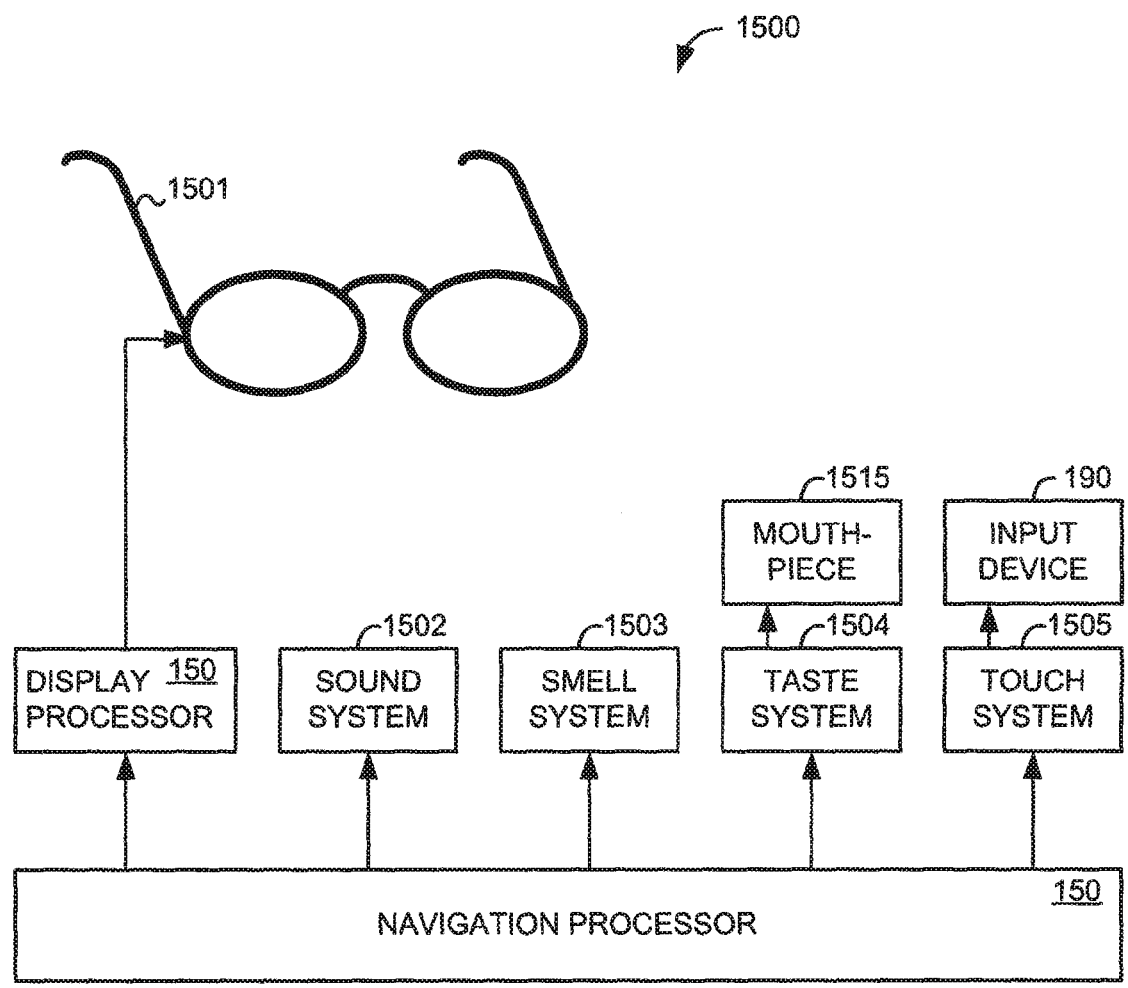
FIG. 15 illustrates a virtual reality system to be optionally used in a medical system utilizing aspects of the present invention.

FIG. 15 illustrates, as an example, a virtual reality system 1500 to be optionally used in the medical system 100 for providing navigation guidance to a surgeon in a virtual reality environment to a target in or adjacent to an anatomical structure in a patient. In the virtual reality system 1500, stereo goggles or glasses 1501, worn by the surgeon, displays either virtual images generated by the virtual camera or real-time images captured by the image capturing element 141 in 3-D as the surgeon moves the medical device 110 through the anatomical structure. As the surgeon approaches each bifurcation in the linked passages of the anatomical structure, an indication of the navigational path to be taken may be provided in one or more of the sense modalities. For example, the navigation processor 160 may perform the steps 801-805 as described in reference to FIG. 8, but in lieu of displaying an arrow in the virtual image 620 on the primary display screen 151, it may provide the navigation indication as an arrow indicating the correct passage to be taken in the stereo glasses 1501 (through the display processor 150) so that the surgeon receives a visual indication of the correct navigational path.

Alternatively or additionally, a navigational path indication may be provided through a sound system 1502 when the medical device 110 approaches a bifurcation by a warning sound being heard if the surgeon directs the distal end 111 of the medical device 110 to enter the wrong passage and/or an assuring sound being heard if the surgeon directs the distal end 111 of the medical device 110 to enter the correct passage. Alternatively or additionally, a navigational path indication may be provided through a smell system 1503 when the medical device 110 approaches a bifurcation by a foul odor being smelt if the surgeon directs the distal end 111 of the medical device 110 to enter the wrong passage and/or pleasing odor being smelt if the surgeon directs the distal end 111 of the medical device 110 to enter the correct passage. Alternatively or additionally, a navigational path indication may be provided through a taste system 1504 when the medical device 110 approaches a bifurcation by a bitter taste being sensed on a mouthpiece 1515 inserted in the surgeon's mouth if the surgeon directs the distal end 111 of the medical device 110 to enter the wrong passage and/or sweet taste being sensed on the mouthpiece 1515 if the surgeon directs the distal end 111 of the medical device 110 to enter the correct passage. Alternatively or additionally, a navigational path indication may be provided through a touch system 1505 when the medical device 110 approaches a bifurcation by a resistive force being felt on the input device 190 if the surgeon directs the distal end 111 of the medical device 110 to enter the wrong passage and/or a forward nudging force being felt on the input device 190 if the surgeon directs the distal end 111 of the medical device 110 to enter the correct passage.

Although the various aspects of the present invention have been described with respect to one or more embodiments, it will be understood that the invention is entitled to full protection within the full scope of the appended claims.

What is claimed is:

1. A medical system comprising:
a memory storing information of a four-dimensional computer model of an anatomical structure of a patient, wherein the four-dimensional computer model includes information of a plurality of three-dimensional computer models of the anatomical structure of the patient, wherein each of the plurality of three-dimensional computer models is for a different point in time than others of the plurality of three-dimensional computer models so that the fourth dimension is time, wherein the plurality of three-dimensional computer models indicate movement of the anatomical structure, wherein each of the plurality of three-dimensional computer models defines a plurality of passages, and wherein each of the plurality of passages has a shape;
a medical device having a flexible body and a plurality of sensors distributed along the length of the flexible body; and
a processor programmed to determine the pose and shape of the flexible body while disposed in a passage of the anatomical structure using information provided by the plurality of sensors at the same point in time and register the medical device to the four-dimensional computer model of the anatomical structure by matching at least the determined shape of the flexible body to a best fitting one of the shapes of one or more potential passages in the four-dimensional computer model of the anatomical structure.

2. The medical system of claim 1, wherein the memory stores information of a navigational path relative to the four-dimensional computer model to a target in the anatomical structure, and wherein the processor is programmed to provide an indication of the navigational path as a steering direction for the medical device after registering the medical device to the four-dimensional computer model.

3. The medical system of claim 2, further comprising;
a display;
wherein the processor is programmed to generate a virtual view within the four-dimensional computer model of an interior of the anatomical structure from a perspective of a distal end of the medical device, and wherein the processor is programmed to display the generated virtual view and an indication of the navigational path on the display.

4. The medical system of claim 3, further comprising:
an image capturing device for capturing images from the perspective of the distal end of the medical device;
wherein the processor is programmed to display the captured images on the display.

5. The medical system of claim 2, further comprising:
a virtual reality environment;
wherein the processor is programmed to generate a virtual view within the virtual reality environment of an interior of the anatomical structure from a perspective of a distal end of the medical device, and wherein the processor is programmed to provide one or more sensory indications of the generated virtual view along with one or more sensory indications of the navigational path.

6. The medical system of claim 5, wherein the one or more sensory indications of the navigational path include one or more of the five senses of hearing, sight, touch, smell, and taste.

7. The medical system of claim 1, wherein the plurality of sensors is a plurality of strain sensors.

8. The medical system of claim 7, wherein the plurality of sensors include sensors employing Rayleigh scattering.

9. The medical system of claim 7, wherein the medical device has one or more optical fibers extending through the flexible body and the plurality of sensors include sensors employing fiber Bragg gratings on the one or more optical fibers.

10. The medical system of claim 1, wherein the anatomical structure is a lung and the one or more potential passages include a trachea, bronchi, and bronchioles.

11. The medical system of claim 1, wherein the anatomical structure is one of a heart, brain, digestive system, circulatory system, and urinary system.

12. The medical system of claim 1, further comprising:
an input device;
one or more actuators coupled to the medical device;
wherein the processor is programmed to command the one or more actuators to move the medical device in response to operator movement of the input device.

13. The medical system of claim 1, wherein the medical device includes one of an endoscope, a catheter, and a medical instrument.

14. The medical system of claim 1, wherein each of the plurality of three-dimensional computer models of the anatomical structure is for a different point in time during a periodic motion of the anatomical structure which includes a circulation within a body of at least one of air and blood.

15. The medical system of claim 1, wherein each of the plurality of three-dimensional computer models of the anatomical structure is for a different point in time during a non-periodic motion of the anatomical structure resulting from a body reaction to a stimulus.

16. A method for registering a flexible medical device disposed within a passage in an anatomical structure of a patient to a four-dimensional computer model of the anatomical structure, wherein the flexible medical device has a plurality of sensors distributed along the length of the flexible medical device, wherein the four-dimensional computer model includes information of a plurality of three-dimensional computer models of the anatomical structure, wherein each of the plurality of three-dimensional computer models is for a different point in time than others of the plurality of three-dimensional computer models so that the fourth dimension is time, wherein the plurality of three-dimensional computer models indicate movement of the anatomical structure, wherein each of the plurality of three-dimensional computer models defines a plurality of passages, and wherein each of the plurality of passages has a shape, the method comprising:
determining a current pose and shape of the flexible medical device using information provided by the plurality of sensors at the same point in time;

registering the flexible medical device to the four-dimensional computer model of the anatomical structure by matching at least the determined shape of the flexible medical device to a best fitting one of the shapes of potential passages in the four-dimensional computer model.

17. A medical system comprising:
a memory storing information of a computer model of an anatomical structure;
a medical device;
an image capturing device for capturing images from a perspective of a distal end of the medical device; and
a processor programmed to periodically perform a global registration of the computer model to the medical device by determining the pose and shape of the medical device while disposed in a passage of the anatomical structure and by matching at least the determined shape of the medical device to a best fitting one of the shapes of one or more potential passages in the computer model of the anatomical structure, followed by performing a local registration of the computer model to the medical device by comparing an image captured by the image capturing device with a plurality of virtual views of the computer model of the anatomical structure, wherein the plurality of virtual views is generated from the perspective of a virtual camera whose pose is initially set at the pose of the distal end of the medical device and then perturbed about the initial pose.

18. The medical system of claim 17, further comprising:
a display;
wherein the memory stores information of a navigational path to a target in the anatomical structure, wherein the processor is programmed to generate a corrected virtual view of the anatomical structure using the periodically performed global and local registration of the computer model of the anatomical structure, and wherein the processor is programmed to cause the captured image, the corrected virtual view, and an indication of the navigational path to be displayed on the display.

19. The medical system of claim 18, wherein the processor is programmed to cause the captured image and the corrected virtual view to be displayed on the display in adjacent windows, and wherein the processor is programmed to cause the indication of the navigational path to be displayed on the display as an arrow indicating a direction to be taken in the corrected virtual view.

20. The medical system of claim 18, further comprising:
an input device;
one or more actuators coupled to the medical device;
wherein the processor is programmed to command the one or more actuators to move the medical device in response to operator movement of the input device.

21. The medical system of claim 17, wherein the medical device includes one of an endoscope, a catheter, and a medical instrument.

22. The medical system of claim 17, wherein the processor is programmed to compensate for motion of the anatomical structure by identifying the motion and employing a trigger associated with a point in the identified motion.

23. The medical system of claim 22, wherein the motion is one or a combination of a periodic motion and non-periodic motion associated with the anatomical structure.

24. The medical system of claim 23, wherein the periodic motion includes a circulation within a body of at least one of air and blood.

25. The medical system of claim 23, wherein the non-periodic motion results from a body reaction to a stimulus.

26. The medical system of claim 17, wherein the memory stores information of a plurality of computer models of the anatomical structure, wherein each of the plurality of computer models corresponds to a different point in time over a period of motion of the anatomical structure, wherein the processor is programmed to register the computer model to the medical device by matching at least the determined shape of the flexible body to a best fitting one of shapes of potential passages in the plurality of computer models, and wherein the computer model used by the processor for generating the plurality of virtual views is the computer model corresponding to the matched passage.

27. The medical system of claim 26, wherein the period of motion is associated with at least one of an identifiable periodic motion and identifiable non-periodic motion.

28. The medical system of claim 27, wherein the identifiable periodic motion includes a circulation within a body of at least one of air and blood.

29. The medical system of claim 27, wherein the identifiable non-periodic motion results from a body reaction to a stimulus.

30. A method for registering a computer model of anatomical structure to a medical device, the method comprising:
periodically performing a global registration of the computer model to the medical device by determining the pose and shape of the medical device while disposed in a passage of the anatomical structure and by matching at least the determined shape of the medical device to a best fitting one of the shapes of one or more potential passages in the computer model of the anatomical structure, followed by performing a local registration of the computer model to the medical device by comparing an image captured by the image capturing device with a plurality of virtual views of the computer model of the anatomical structure, wherein the plurality of virtual views is generated from the perspective of a virtual camera whose pose is initially set at the pose of the distal end of the medical device and then perturbed about the initial pose.

* * * * *